United States Patent [19]

Seto et al.

[11] Patent Number: 4,885,284

[45] Date of Patent: Dec. 5, 1989

[54] DIHYDROPYRIDINE-5-PHOSPHONIC ACID CYCLIC PROPYLENE ESTER

[75] Inventors: Kiyotomo Seto, Funabashi; Sakuya Tanaka, Hasuda; Ryozo Sakoda, Kashiwa, all of Japan

[73] Assignee: Nissan Chemical Industries Ltd., Tokyo, Japan

[21] Appl. No.: 851,158

[22] Filed: Apr. 14, 1986

[30] Foreign Application Priority Data

Jan. 22, 1986 [JP] Japan .................................. 61-11255
Jan. 23, 1986 [JP] Japan .................................. 61-12755

[51] Int. Cl.[4] ...................... A61K 31/675; C07F 9/58; C07F 9/65; C07F 9/40
[52] U.S. Cl. ........................................ 514/89; 546/21; 514/85; 544/337; 558/178; 560/172
[58] Field of Search ........................... 546/21; 544/337; 514/85, 89

[56] References Cited

U.S. PATENT DOCUMENTS 4,535,073 8/1985 Kimura et al. ........................ 514/89
4,576,934 3/1986 Seto et al. ............................ 514/89 X

FOREIGN PATENT DOCUMENTS 0141221 5/1985 European Pat. Off. .
0141222 5/1985 European Pat. Off. .
4203193 3/1988 U.S.S.R. .
2157695 10/1985 United Kingdom ................. 546/21

OTHER PUBLICATIONS

Fujimoto et al., European Journal of Pharmacology, pp. 243-254, (1986).
Loev et al., J. Med. Chem., vol. 17(9), 1974, pp. 956-965.
Merck Index, 10th Ed., (1983), p. 164, Entry 1160.

*Primary Examiner*—Nicholas S. Rizzo
*Assistant Examiner*—E. Bernhardt

*Attorney, Agent, or Firm*—Oblon, Spivak, McClelland, Maier & Neustadt

[57] ABSTRACT

A compound of the formula:

(I)

wherein each of $R^1$, $R^2$, $R^3$, $R^4$, $R^5$ and $R^6$ which may be the same or different, is hydrogen or $C_1$-$C_4$ alkyl; one of $X^1$ and $X^2$ is nitro, fluroine, chlorine, difluoromethyoxy or trifluoromethyl and the other is hydrogen, or both of $X^1$ and $X^2$ are chlorine; and Y is $$-A-N\begin{matrix}Ar^1\\(CH_2)_mAr^2\end{matrix}$$

wherein A is C-$C_6$ alkylene, each of $Ar^1$ and $Ar^2$ which may be the same or different, is phenyl which may be substituted by chlorine, fluorine or $C_1$-$C_3$ alkoxy, and m is an integer of from 0 to 4, or Y is $$-A-N\bigg\langle\phantom{x}\bigg\rangle NCH\begin{matrix}Ar^1\\Ar^2\end{matrix}$$

wherein A, $Ar^1$ and $Ar^2$ are as defined above when that both $X^1$ and $X^2$ are chlorine; or a pharmaceutically acceptable salt thereof.

9 Claims, No Drawings

DIHYDROPYRIDINE-5-PHOSPHONIC ACID CYCLIC PROPYLENE ESTER

BACKGROUND OF THE INVENTION

1. Field of the Invention

The present invention relates to a novel 1,4-dihydropyridine-5-phosphonic acid cyclic propylene ester, a process for the preparation thereof, and an antihypertensive agent or coronary or cerebral vasodilator composition containing the novel ester or its pharmaceutically acceptable salt.

2. Description of the Prior Art 1,4-Dihydropyridines-5-phosphonic acid esters are known to be useful for the medical treatment of coronary heart diseases, cerebral diseases, hypertension or arrhythmia, as they are capable of inhibiting the contraction of smooth muscle and cardiac muscle by calcium antagonistic effects. (See European Patent Publications EP 0159040A and EP 0121117A which corresponds to U.S. Pat. No. 4,535,073.)

SUMMARY OF THE INVENTION

The present invention provides a novel compound of the formula:

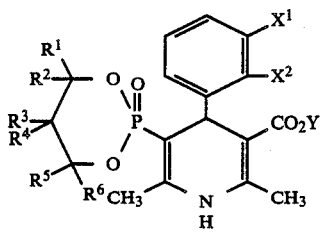

wherein each of $R^1$, $R^2$, $R^3$, $R^4$, $R^5$ and $R^6$ which may be the same or different, is hydrogen or $C_1$-$C_4$ alkyl; one of $X^1$ and $X^2$ is nitro, fluorine, chlorine, difluoromethoxy or trifluoromethyl and the other is hydrogen, or both of $X^1$ and $X^2$ are chlorine; and Y is

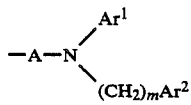

wherein A is $C_2$-$C_6$ alkylene, each of $Ar^1$ and $Ar^2$ which may be the same or different, is phenyl which may be substituted by chlorine, fluorine or $C_1$-$C_3$ alkoxy, and m is an integer of from 0 to 4, or Y is

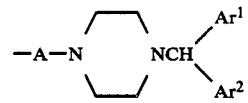

wherein A, $Ar^1$ and $Ar^2$ are as defined above when that both $X^1$ and $X^2$ are chlorine; or a pharmaceutically acceptable salt thereof.

Some of the compounds of the formula I have optical isomers or diastereomers. The present invention covers such optical isomers and diastereomers.

The present invention also provides an antihypertensive agent or coronary or cerebral vasodilator composition comprising an effective amount of the compound of the formula I or its pharmaceutically acceptable salt and a pharmaceutically acceptable diluent or carrier.

DETAILED DESCRIPTION OF THE PREFERRED EMBODIMENTS

The substituents in the formula I of the compounds of the present invention will be further illustrated as hereunder.

Examples of $R^1$, $R^2$, $R^3$, $R^4$, $R^5$ and $R^6$ in the formula I are hydrogen, methyl, ethyl, n-propyl and i-propyl.

And preferred examples of

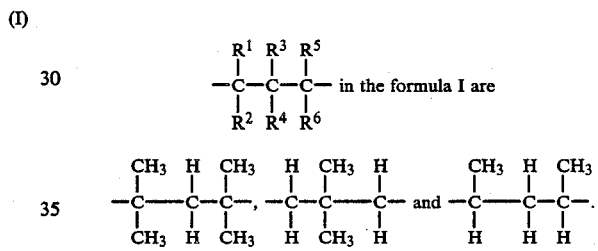

Examples of $X^1$ and $X^2$ in the formula I are hydrogen, nitro, chlorine, fluorine, difluoromethoxy and trifluoromethyl.

Examples of A are —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, —CH(CH$_3$)CH$_2$—, —CH(CH$_3$)CH(CH$_3$)—, —C(CH$_3$)$_2$CH$_2$— and —CH$_2$C(CH$_3$)$_2$CH$_2$—. Preferred examples of A are —CH$_2$CH$_2$—, —CH$_2$CH$_2$CH$_2$— and —CH(CH$_3$)CH$_2$—.

Examples of $Ar^1$ and $Ar^2$ are phenyl, fluorophenyl, chlorophenyl, dichlorophenyl, methoxyphenyl, dimethoxyphenyl, trimethoxyphenyl, ethoxyphenyl and diethoxyphenyl.

The compound of the present invention can be prepared in accordance with the flow chart of the following Scheme 1.

Scheme 1

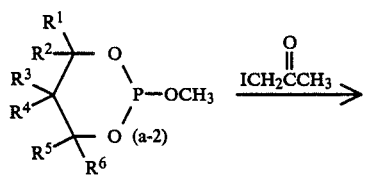

Scheme 1 -continued

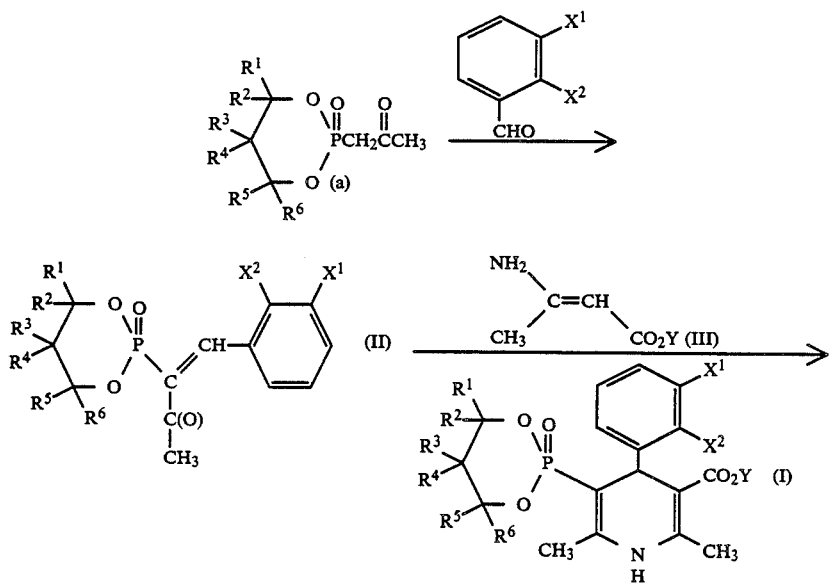

In Scheme 1, $R^1$, $R^2$, $R^3$, $R^4$, $R^5$, $R^6$, $X^1$, $X^2$ and Y have the same meanings as defined with respect to the formula I.

The acetonyl phosphonic acid cyclic propylene ester (a) can be prepared by means of a conventional technique (see D. W. White, J. Am. Chem. Soc., 92, 7125-7135 (1970)). Namely, as shown by Scheme 1, it is obtainable by the reaction of a 1-methoxy-1-phospha-2,6-dioxacyclohexane derivative (a-2) with iodoacetone.

The compounds of the present invention of the formula I can be obtained by reacting the compound of the formula II with the compound of the formula III in an inert solvent in accordance with the above Scheme 1. The starting compound of the formula II is obtainable by reacting the acetonyl phosphonic acid cyclic ester (a) with a benzaldehyde derivative by means of a conventional technique. Likewise, the starting compound of the formula III can readily be obtained by reacting the corresponding carbonyl compound with ammonia. The starting compound of the formula III may be formed in the reaction system simply by mixing the corresponding carbonyl compound with ammonia and is not necessarily required to be isolated.

The inert solvent includes an alcohol solvent such as methanol, ethanol, propanol or isopropanol, an ether solvent such as 1,2-dimethoxyethane or THF, an aromatic hydrocarbon solvent such as benzene, toluene or xylene, a nitrile solvent such as acetonitrile or benzonitrile, an amide solvent such as DAM, DMF or N-methylpyrrolidone, a sulfoxide solvent such as DMSO or sulfolane, an ester solvent such as ethyl acetate or butyrolactone, or pyridine.

The reaction is usually conducted at a temperature of from room temperature to 200° C., preferably from 60° to 140° C., for from 1 to 100 hours, preferably from 5 to 20 hours.

As mentioned above, the compounds of the present invention are not only capable of inhibiting the contraction of smooth muscle and cardiac muscle by the calcium antagonistic effects but also antihypertensively effective when administered orally. Thus, they are useful for the medical treatment of the coronary heart diseases, cerebral diseases or hypertension of mammals.

The oral toxicities of the compounds of the present invention are unexpectedly low.

The unexpectedly long durations of the antihypertensive activities of the compounds of the present invention have been observed.

Thus, the present invention provides an anti-hypertensive agent or coronary or cerebral vasodilator composition comprising an effective amount of the compound of the formula I or its pharmaceutically acceptable salt, and a pharmaceutically acceptable diluent or carrier. Such a composition may also be formulated into a veterinary composition by combining the compound of the present invention with a veterinarily acceptable diluent or carrier.

Such compositions may be used in the form suitable for oral administration, e.g. tablets or capsules, in the form suitable for transdermal administration, e.g. ointments or plasters, in the form suitable for inhalation, e.g. aerosols or solutions suitable for spraying, in the form suitable for injection administration, e.g. a sterilized aqueous solution, or in the form of a suppository suitable for use in anus, vagina or rectum.

The compositions of the present invention usually contain the compound of the formula I in an amount of from about 0.1 to about 99.5% by weight, preferably from about 0.5 to about 95% by weight, based on the total weight of the composition.

The compounds of the present invention or the compositions of the present invention may be used in combination with other pharmaceutically or veterinarily active compounds. Further, the composition of the present invention may contain a plurality of the compounds of the formula I.

The daily dose of the compounds of the formula I may be varied depending upon the type and the condition of the desease to be cured and the type of the patient (the age, sex, sensitivity, etc.). In the case of the intravenous administration, the daily dose is usually from 0.0001 to 10 mg, preferably from 0.0005 to 1 mg, of the active ingredient per 1 kg of the body weight.

Likewise, in the case of the oral or transdermal administration, the daily dose is usually from 0.001 to 100 mg of the active ingredient per 1 kg of the body weight. Further, the daily dose in the case of the administration in the form of a suppository to e.g. a vagina or rectum, is usually from 0.001 to 200 mg, preferably from 0.005 to 100 mg, of the active ingredient per 1 kg of the body weight. The content of the active ingredient in an aerosol, is usually from 0.1 to 10% by weight, preferably from 0.1 to 2% by weight. Such a daily dose may be divided for administration twice or more times per day.

The above-mentioned compositions containing the compounds of the formula I may be prepared by a conventional method, and a conventional excipient may be incorporated therein.

The present invention will be now described in further detail with reference to Working Examples, Test Examples and various formulations. However, it should be understood that the present invention is by no means restricted by these specific Examples.

EXAMPLES

Test 1: Pharmacological activities of the compounds of the present invention

(1) Calcium antagonistic effects 10 mm in situ length of taenia caecum of guinea pig was suspended at a tension of 1 g in a 20 ml organ bath filled with a physiological salt solution (NaCl: 135 mM, KCl: 5 mM etc.).

This solution was bubbled with a gas mixture of 95% $O_2 - 5\%$ $CO_2$ and kept at 37° C. Then, the preparation was depolarized by a $K^+$ rich solution (NaCl: 40 mM, KCl: 100 mM). After 10–20 minutes equilibration period, 10 mM of $CaCl_2$ was added to the bathing solution. The contraction was produced, and then the test compound applied cumulatively. The relaxation produced was expressed as percentage of the maximum relaxation produced by $10^{-4}M$ papaverine, and the concentration of the compound producing 50% relaxation, i.e. $ID_{50}$ (M), was calculated. The values of $pID_{50}$ ($pID_{50} = -\log [ID_{50}]$, are summarized in Table 1.

(2) Antihypertensive effects

After oral administration of the test compound dissolved in a $H_2O$-PEG 400 solvent mixture ($H_2O$:PEG 400 (w/w)=1:3) to the male spontaneously hypertensive rat (SHR), the systolic blood pressure was measured at 2, 4, 6 and 8 hours after the administration of the test compounds by a tail cuff method. Prior to the measurement, rats were warmed at 50° C. for five minutes. The effectively antihypertensive activities were observed also at 8 hours after the administraton of the test compounds. The results are summarized in Table 1.

Test 2: Acute toxicity test ddY mice (♂, 4 weeks old) were divided into groups of five mice and the test compound dissolved in purified water was administered orally (5% solution) (p.o) to the male ddY mice.

After seven days, $LD_{50}$ values were calculated from the dead rats recorded in the individual dosage groups by the method of Litchfield-Wilcoxon. The results are shown in Table 1.

TABLE 1

Calcium antagonistic effect, antihypertensive effect and $LD_{50}$ value of the compound of the present invention.

| Compound | $pID_{50}$ | Antihypertensive effect Dose (mg/kg) | Antihypertensive effect Maximum decrease (%) | $LD_{50}$ (mg/kg) |
|---|---|---|---|---|
| Hydrochloride of Example 1 | 8.17 | 15 | 36 | >600 |
| Dihydrochloride of Example 2 | 7.01 | 10 | 37 | >400 |
| Dihydrochloride of Example 3 | 6.76 | 15 | 36 | >400 |
| Hydrochloride of Example 4 | 6.90 | 20 | 38 | >300 |
| Hydrochloride of Example 5 | — | 10 | 40 | >300 |
| Hydrochloride of Example 6 | 6.98 | 10 | 28 | >300 |
| Hydrochloride of Example 7 | 8.17 | 15 | 34 | >600 |

EXAMPLE 1

Synthesis of 2-(N-benzyl-N-phenylamino)ethyl 5-(2,2-dimethylpropylenedioxyphosphinyl)-2,6-dimethyl-1,4-dihydro-4-(3-nitrophenyl)pyridine-3-carboxylate

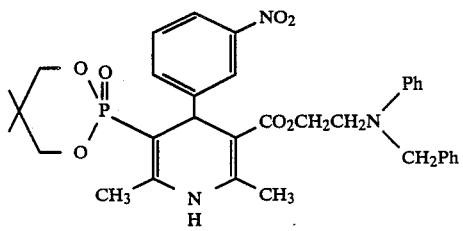

14.7 g of 2,2-dimethylpropylene α-(3-nitrobenzylidene)acetonylphosphonate and 13.4 g of 2-(N-benzyl-N-phenyl)ethyl 3-aminocrotonate were dissolved in 50 ml of toluene, and the solution was refluxed for 10 hours. Then, the precipitate was collected by filtration and was recrystallized from ethyl acetate, whereby the above-identified compound was obtained as yellow crystal (mp 155°–156° C.). In a similar manner, compounds of Example 1 to 12 were obtained. The characteristics and the mass spectral data of the compounds thus obtained are shown in Table 2.

TABLE 2

![structure](parent compound with X1, X2 on phenyl ring, CO2Y, CH3, NH, Z, CH3 substituents)

| Example No. | $X^1$ | $X^2$ | Y | Z | Yield (%) | Characteristics (mp, °C.) | MS, m/e (intensity ratio) |
|---|---|---|---|---|---|---|---|
| 1 | $NO_2$ | H | CH₂CH₂N(Ph)(CH₂—Ph) | 6-membered cyclic phosphate (P=O with two O, gem-dimethyl) | 45 | Yellow solid (155-156) | 196(61), 209(100), 631(7, M⁺) |
| 2 | Cl | Cl | CH₂CH₂N(piperidine with N-Ph)  | 6-membered cyclic phosphate | 60 | Yellow solid (206-207) | 44(100), 167(32), 408(5) |
| 3 | Cl | Cl | CH₂CH₂CH₂N(piperidine with N-CH(4-F-Ph)₂) | 6-membered cyclic phosphate | 55 | Yellow amorphous | 126(81), 203(100), 301(38), 773(20, M⁺) |
| 4 | $NO_2$ | H | CH(CH₃)CH₂N(Ph)(CH₂—Ph) | 6-membered cyclic phosphate with tetramethyl | 40 | Yellow oily substance | 196(100), 495(5), 656(3), 673(2, M⁺) |
| 5 | $NO_2$ | H | CH₂CH₂N(Ph)(CH₂—Ph) | 6-membered cyclic phosphate with tetramethyl | 69 | Yellow oily substance | 81(100), 196(93), 481(15) |

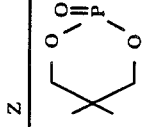
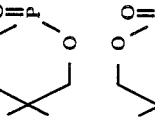
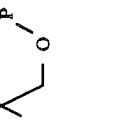
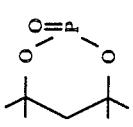
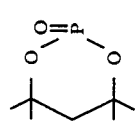

TABLE 2-continued

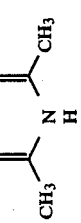

| Example No. | $X^1$ | $X^2$ | Y | Z | Yield (%) | Characteristics (mp, °C.) | MS, m/e (intensity ratio) |
|---|---|---|---|---|---|---|---|
| 6 | Cl | Cl | CHCH$_2$N—Ph<br>\|  \|<br>CH$_3$  CH$_2$—Ph |  | 46 | Yellow oily substance | 91(67), 223(100), 669(2, M$^+$) |
| 7 | NO$_2$ | H | Ph<br>\|<br>CH$_2$CH$_2$N<br>\|<br>CH$_2$—Ph | 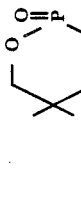 | 81 | Yellow oily substance | 186(50), 209(100), 631(11, M$^+$) |
| 8 | Cl | Cl | Ph<br>\|<br>CH$_2$CH$_2$N<br>\|<br>Ph | 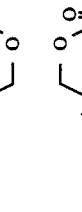 | 68 | Pale yellow solid (131) | 182(29), 195(100), 640(5, M$^+$) |
| 9 | Cl | Cl | Ph<br>\|<br>(CH$_2$)$_3$N  NCH<br>\|<br>Ph | 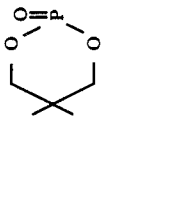 | 74 | Pale yellow solid (158) | 125(100), 167(29), 428(39), 737(18, M$^+$) |
| 10 | Cl | Cl | [4-F-C$_6$H$_4$]<br>\|<br>CH$_2$CH$_2$N  NCH<br>\|<br>[4-F-C$_6$H$_4$] | 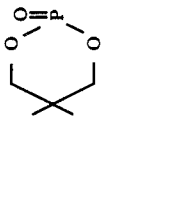 | 67 | Pale yellow solid (141) | 203(100), 300(44), 759(12, M$^+$) |

TABLE 2-continued

[Structure: dihydropyridine with X¹, X² on phenyl ring, CO₂Y, two CH₃ groups, two Z groups, N-H]

| Example No. | X¹ | X² | Y | Z | Yield (%) | Characteristics (mp, °C.) | MS, m/e (intensity ratio) |
|---|---|---|---|---|---|---|---|
| 11 | Cl | Cl | CHCH₂N—Ph<br>\|<br>CH₃  CH₂Ph | [1,3,2-dioxaphosphorinane 2-oxide with gem-dimethyl] | 84 | Yellow oily substance | 223(100), 408(5), 668(2, M⁺) |
| 12 | H | OCHF₂ | [piperazine: CH₂CH₂N—NCH(Ph)(Ph) / CH₂CH₂N] | [1,3,2-dioxaphosphorinane 2-oxide with gem-dimethyl] | 75 | Colorless solid (214) | 167(100), 278(63), 426(54), 721(46, M⁺) |

Now, examples will be given for various formulations containing the compound of the formula I.

TABLETS

Composition (1,000 tablets)

| | |
|---|---|
| Hydrochloride of the compound of the Example 1 | 5.0 (g) |
| Lactose | 190.0 |
| Corn starch | 75.0 |
| Crystal cellulose powder | 25.0 |
| Methyl cellulose | 3.0 |
| Magnesium stearate | 2.0 |
| | 300.0 |

The above ingredients in the respective amounts were introduced into a twin shell mixer and uniformly mixed. This powder mixture was tableted by a direct compression method to obtain tablets having a weight of 300 mg per tablet.

CAPSULES

Composition (1,000 capsules)

| | |
|---|---|
| Hydrochloride of the Compound of the Example 1 | 5 (g) |
| Corn starch | 145 |
| Crystal cellulose powder | 145 |
| Magnesium stearate | 5 |
| | 300 |

The above ingredients in the respective amounts were introduced into a twin shell mixer and uniformly mixed. This powder mixture was packed in hard gelatin capsules in an amount of 300 mg per capsule.

POWDER

Composition:

| | |
|---|---|
| Hydrochloride of the compound of the Example 1 | 1.0 (g) |
| Lactose | 88.0 |
| Crystal cellulose powder | 10.0 |
| Methyl cellulose | 1.0 |
| | 100.0 |

The above ingredients in the respective amounts were introduced into a twin shell mixer and uniformly mixed to obtain a powder.

SYRUP

Composition (2% syrup):

| | |
|---|---|
| Hydrochloride of the compound of the Example 1 | 2.0 (g) |
| Sugar | 30.0 |
| Glycerin | 5.0 |
| Flavoring agent | 0.1 |
| 96% ethanol | 10.0 |
| Methyl p-hydroxybenzoate | 0.03 |
| Purified water | to make 100.0 g |

The sugar and the hydrochloride of the compound of Example 1 were dissolvd in 60 g of warm water, and after cooling the solution, a solution of the flavoring agent in glycerin and ethanol was added. Then, wafter was added to this mixture to bring the total amount to 100.0 g.

What is claimed is:

1. A compound of the formula:

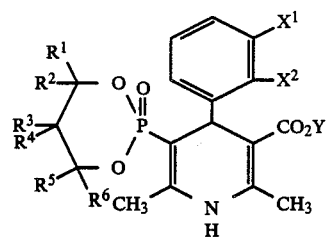

wherein each of $R^1$, $R^2$, $R^3$, $R^4$, $R^5$ and $R^6$ which may be the same or different, is hydrogen or $C_1-C_4$ alkyl; one of $X^1$ and $X^2$ is nitro, fluorine, chlorine, difluoromethoxy or trifluoromethyl and the other is hydrogen; and Y is

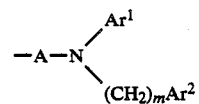

where A is $C_2-C_6$ alkylene, each of $Ar^1$ and $Ar^2$ which may be the same or different, is phenyl which may be substituted by chlorine, fluorine or $C_1-C_3$ alkoxy, and m is zero or an integer up to 4; or a pharmaceutically acceptable salt thereof.

2. The compound of claim 1, wherein one of $X^1$ and $X^2$ is nitro or chlorine and the other is hydrogen.

3. The compound of claim 2, wherein each of $R^1$, $R^2$, $R^3$, $R^4$, $R^5$ and $R^6$ which may be the same or different, is hydrogen or methyl.

4. The compound of claim 3, wherein A is —CH$_2$CH$_2$—, —(CH$_2$)$_3$— or —CH(CH$_3$)CH$_2$—, and m is one.

5. The compound of claim 4, wherein each of $Ar^1$ and $Ar^2$ which may be the same or different, is phenyl or p-fluorophenyl.

6. The compound of claim 5, wherein
—C($R^1$)($R^2$)C($R^3$)($R^4$)C($R^5$)($R^6$)— is
—CH$_2$C(CH$_3$)$_2$CH$_2$—,
—C(CH$_3$)$_2$CH$_2$C(CH$_3$)$_2$— or
—CH(CH$_3$)CH$_2$CH(CH$_3$)—.

7. The compound of claim 1, having the formula:

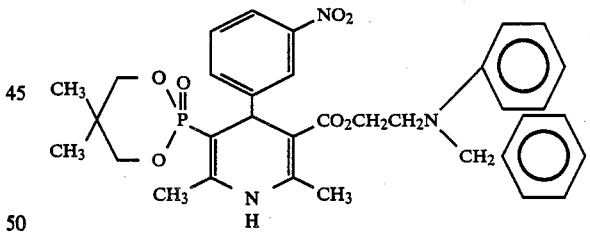

or a pharmaceutically acceptable salt thereof.

8. The compound of claim 1, which is 1-methyl-2-(N-benzyl-N-phenylamino)ethyl 5-(1,1,3,3,-tetramethyl-propylenedioxphosphinyl)-2,6-dimethyl-1,4-dihydro-4-(3-nitrophenyl)-pyridine-3-carboxylate, 2-(N-benzyl-N-phenylamino)ethyl 5-(1,1,3,3-tetramethyl-propylenedioxyphosphinyl)-2,6-dimethyl-1,4-dihydro-4-(3-nitrophenyl)-pyridine-3-carboxylate, 2-(N-benzyl-N-phenylamino)ethyl 5-(1(R), 3(R)-dimethylpropylene-dioxyphosphinyl)-2,6-dimethyl-1,4-dihyro-4-(3-nitrophenyl)-pyridine-3-carboxylate, or a pharmaceutically acceptable salt thereof.

9. An antihypertensive, coronary or cerebral vasodilator composition comprising
(a) an antihypertensive, coronary or cerebral vasodilator effective amount of the compound of claim 1; and
(b) a pharmaceutically acceptable diluent or carrier.

* * * * *